(12) United States Patent
Poruthoor

(10) Patent No.: US 11,123,949 B2
(45) Date of Patent: Sep. 21, 2021

(54) TEXTURED NONWOVEN LAMINATE

(71) Applicant: Kimberly-Clark Worldwide, Inc., Neenah, WI (US)

(72) Inventor: Simon K. Poruthoor, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 67 days.

(21) Appl. No.: 15/517,533

(22) PCT Filed: Nov. 25, 2014

(86) PCT No.: PCT/US2014/067325
§ 371 (c)(1),
(2) Date: Apr. 7, 2017

(87) PCT Pub. No.: WO2016/085468
PCT Pub. Date: Jun. 2, 2016

(65) Prior Publication Data
US 2017/0305105 A1   Oct. 26, 2017

(51) Int. Cl.
*B32B 5/02* (2006.01)
*B32B 38/18* (2006.01)
(Continued)

(52) U.S. Cl.
CPC ............. *B32B 5/022* (2013.01); *A47L 13/16* (2013.01); *B32B 3/12* (2013.01); *B32B 3/26* (2013.01);
(Continued)

(58) Field of Classification Search
CPC .. B32B 5/022; B32B 3/26; B32B 3/28; B32B 3/30; B32B 3/12; B32B 2553/026;
(Continued)

(56) References Cited

U.S. PATENT DOCUMENTS

| 2,585,915 A | 2/1952 | Chavannes |
| 2,776,451 A | 1/1957 | Chavannes |

(Continued)

FOREIGN PATENT DOCUMENTS

WO   WO 2005/065516 A2   7/2005

OTHER PUBLICATIONS

Abstract of Japanese Patent—JP2001341219, Dec. 11, 2001, 2 pages.
(Continued)

*Primary Examiner* — Jasper Saberi
(74) *Attorney, Agent, or Firm* — Dority & Manning, P.A.

(57) ABSTRACT

A textured laminate that contains a coform nonwoven web formed from a matrix of synthetic fibers and an absorbent material is provided. The coform web is positioned adjacent to a cellular film that includes a plurality of cavities encapsulating a gas (e.g., air). By selectively controlling various aspects of the coform web, film, and the particular manner in which the film and coform web are laminated together, the present inventors have discovered that the resulting laminate can achieve an increased bulk that remains relatively stable even in a wet condition. Thus, the resulting laminate can be readily employed in a wet wipe without losing its bulk and overall texture.

19 Claims, 4 Drawing Sheets

(51) Int. Cl.

| | | |
|---|---|---|
| *B32B 37/00* | (2006.01) | |
| *B32B 37/24* | (2006.01) | |
| *B32B 7/05* | (2019.01) | |
| *B32B 3/30* | (2006.01) | |
| *B32B 3/12* | (2006.01) | |
| *A47L 13/16* | (2006.01) | |
| *B65D 81/03* | (2006.01) | |
| *B32B 3/28* | (2006.01) | |
| *B32B 3/26* | (2006.01) | |
| *B32B 5/18* | (2006.01) | |
| *B32B 37/14* | (2006.01) | |
| *B32B 27/04* | (2006.01) | |
| *B32B 27/08* | (2006.01) | |
| *B08B 1/00* | (2006.01) | |
| *A47K 10/32* | (2006.01) | |
| *A61K 8/02* | (2006.01) | |

(52) U.S. Cl.
CPC ............ *B32B 3/28* (2013.01); *B32B 3/30* (2013.01); *B32B 5/18* (2013.01); *B32B 7/05* (2019.01); *B32B 37/0046* (2013.01); *B32B 37/14* (2013.01); *B32B 37/24* (2013.01); *B32B 38/1858* (2013.01); *B65D 81/03* (2013.01); *A47K 2010/3266* (2013.01); *A61K 8/0208* (2013.01); *B08B 1/006* (2013.01); *B32B 27/04* (2013.01); *B32B 27/08* (2013.01); *B32B 2262/0253* (2013.01); *B32B 2307/728* (2013.01); *B32B 2432/00* (2013.01); *B32B 2553/026* (2013.01)

(58) Field of Classification Search
CPC ..... B32B 2432/00; B65D 81/03; A47L 13/16; A47K 2010/3266; A61K 8/0208; B08B 1/006
See application file for complete search history.

(56) References Cited

U.S. PATENT DOCUMENTS

| | | |
|---|---|---|
| 2,776,452 A | 1/1957 | Chavannes |
| 3,026,231 A | 3/1962 | Chavannes |
| 3,208,898 A | 9/1965 | Chavannes et al. |
| 3,285,793 A | 11/1966 | Chavannes |
| 3,338,992 A | 8/1967 | Kinney |
| 3,341,394 A | 9/1967 | Kinney |
| 3,405,020 A | 10/1968 | Chavannes |
| 3,416,984 A | 12/1968 | Chavannes et al. |
| 3,502,538 A | 3/1970 | Petersen |
| 3,502,763 A | 3/1970 | McBride |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 4,100,324 A | 7/1978 | Anderson et al. |
| 4,327,730 A | 5/1982 | Sorensen |
| 4,340,563 A | 7/1982 | Appel et al. |
| 4,614,000 A | 9/1986 | Mayer |
| 4,789,592 A | 12/1988 | Taniguchi et al. |
| 4,795,668 A | 1/1989 | Krueger et al. |
| 5,057,361 A | 10/1991 | Sayovitz et al. |
| 5,057,368 A | 10/1991 | Largman et al. |
| 5,069,970 A | 12/1991 | Largman et al. |
| 5,108,820 A | 4/1992 | Kaneko et al. |
| 5,116,444 A | 5/1992 | Fox |
| 5,162,074 A | 11/1992 | Hills |
| 5,277,976 A | 1/1994 | Hogle et al. |
| 5,336,552 A | 8/1994 | Strack et al. |
| 5,350,624 A | 9/1994 | Georger et al. |
| 5,382,400 A | 1/1995 | Pike et al. |
| 5,466,410 A | 11/1995 | Hills |
| 5,508,102 A | 4/1996 | Georger et al. |
| 5,540,332 A | 7/1996 | Kopacz et al. |
| 5,667,635 A | 9/1997 | Win et al. |
| 5,785,179 A | 7/1998 | Buczwinski et al. |
| 5,888,524 A | 3/1999 | Cole |
| 5,964,351 A | 10/1999 | Zander |
| 6,028,018 A | 2/2000 | Amundson et al. |
| 6,030,331 A | 2/2000 | Zander |
| 6,158,614 A | 12/2000 | Haines et al. |
| 6,183,838 B1 | 2/2001 | Kannankeril |
| 6,200,669 B1 | 3/2001 | Marmon et al. |
| 6,269,969 B1 | 8/2001 | Huang et al. |
| 6,269,970 B1 | 8/2001 | Huang et al. |
| 6,273,359 B1 | 8/2001 | Newman et al. |
| 6,440,437 B1 | 8/2002 | Krzysik et al. |
| 6,852,391 B2 | 2/2005 | Kannankeril |
| 7,168,932 B2 | 1/2007 | Lassig et al. |
| 7,879,172 B2 | 2/2011 | Kopacz et al. |
| 8,557,169 B2 | 10/2013 | Gross et al. |
| 2002/0192268 A1 | 12/2002 | Alwattari et al. |
| 2003/0211802 A1 | 11/2003 | Keck et al. |
| 2005/0148261 A1 | 7/2005 | Close et al. |
| 2007/0020440 A1 | 1/2007 | Wong et al. |
| 2007/0045903 A1* | 3/2007 | Day ................ B29C 51/225 264/454 |
| 2007/0049153 A1 | 3/2007 | Dunbar et al. |
| 2011/0152164 A1* | 6/2011 | Close ................ C11D 17/049 510/441 |
| 2012/0227203 A1* | 9/2012 | Ouellette ............. B32B 5/022 15/209.1 |

OTHER PUBLICATIONS

Abstract of Japanese Patent—JP2013078392, May 2, 2013, 1 page.
Machine Translation of JPH04163352, Jun. 8, 1992, 6 pages.
International Search Report and Written Opinion for PCT/US2014/067325 dated Jul. 20, 2015, 12 pages.

* cited by examiner

TEXTURED NONWOVEN LAMINATE

RELATED APPLICATION

The present application is the national stage entry of International Patent Application No. PCT/US2014/067325 having a filing date of Nov. 25, 2014, which is incorporated herein in its entirety by reference thereto.

BACKGROUND OF THE INVENTION

Nonwoven webs that contain an absorbent material (e.g., pulp fibers) are often used as an absorbent layer in a wide variety of applications, including wet wipes. A common problem with many conventional nonwoven materials is that they lack enough bulk or thickness to enable a user to easily handle and manipulate the web during wiping or cleaning. This becomes particularly problematic when the substrate is wet as most absorbent materials tend to become more compressed in this state. One solution to this problem has been to simply add more material to the nonwoven web so that the desired bulk is achieved. Unfortunately, this can result in a significant increase in the material and transportation cost of the substrate. As such, a need currently exists for an improved nonwoven web for use in a variety of applications.

SUMMARY OF THE INVENTION

In accordance with one embodiment of the present invention, a nonwoven laminate is disclosed that comprises a cellular film containing a plurality of spaced apart cavities that encapsulate a gas. A coform nonwoven web is positioned adjacent to the cellular film, wherein the coform nonwoven web comprises a composite matrix formed from a combination of synthetic fibers and an absorbent material. If desired, the cellular film can be positioned between multiple coform nonwoven webs. In another embodiment, a wipe may be formed that comprises the nonwoven laminate.

In one embodiment, the nonwoven laminate may be formed by a method that comprises merging together a stream of the absorbent material with a stream of the synthetic fibers to form a composite stream; and thereafter, collecting the composite stream on a surface of the cellular film to form the nonwoven laminate. In another embodiment, the nonwoven laminate may be formed by a method that comprises placing a first film layer into contact with a patterned embossing roll and applying a suctional force to bias the first film layer against the roll and form a plurality of concave sections therein; placing a second film layer into contact with the first film layer to entrap a gas in the concave sections and form the cavities; and bonding the coform nonwoven web to the second film layer. In yet another embodiment, a method of forming a nonwoven laminate is disclosed that comprises providing a first laminate and a second laminate, each of which contains a coform nonwoven web and a film; placing the coform nonwoven web of the first laminate into contact with a patterned embossing roll and applying a suctional force to bias the first laminate against the roll and form a plurality of concave sections in the film of the first laminate; and placing the second laminate into contact with the film of the first laminate to entrap a gas in the concave sections and form cavities that encapsulate a gas.

Other features and aspects of the present invention are described in more detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
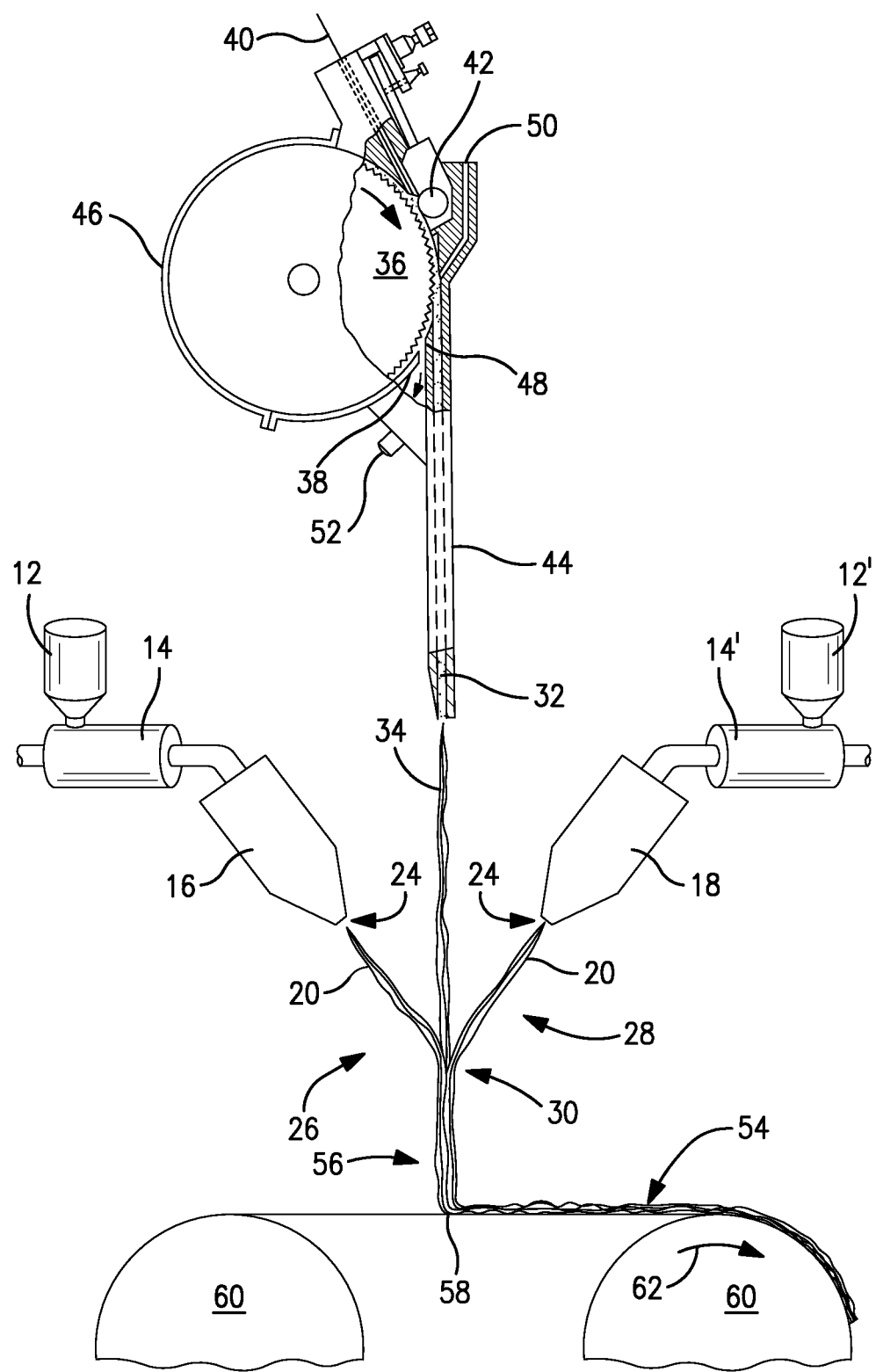
FIG. 1 is a schematic illustration one embodiment of a method for forming a coform web that may be employed in the present invention.

Repeat use of reference characters in the present specification and drawings is intended to represent same or analogous features or elements of the invention.

DETAILED DESCRIPTION OF REPRESENTATIVE EMBODIMENTS

Definitions

As used herein the term "nonwoven web" generally refers to a web having a structure of individual fibers or threads which are interlaid, but not in an identifiable manner as in a knitted fabric. Examples of suitable nonwoven fabrics or webs include, but are not limited to, meltblown webs, spunbond webs, bonded carded webs, airlaid webs, coform webs, hydraulically entangled webs, and so forth.

As used herein, the term "meltblown web" generally refers to a nonwoven web that is formed by a process in which a molten thermoplastic material is extruded through a plurality of fine, usually circular, die capillaries as molten fibers into converging high velocity gas (e.g., air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin, et al. Generally speaking, meltblown fibers may be microfibers that are substantially continuous or discontinuous, generally smaller than 10 micrometers in diameter, and generally tacky when deposited onto a collecting surface.

As used herein, the term "spunbond web" generally refers to a web containing small diameter substantially continuous fibers. The fibers are formed by extruding a molten thermoplastic material from a plurality of fine, usually circular, capillaries of a spinneret with the diameter of the extruded fibers then being rapidly reduced as by, for example, educative drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al. Spunbond fibers are generally not tacky when they are deposited onto a collecting surface. Spunbond fibers may sometimes have diameters less than about 40 micrometers, and are often between about 5 to about 20 micrometers.

DETAILED DESCRIPTION

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

Generally speaking, the present invention is directed to a textured laminate that contains a coform nonwoven web that is formed from a matrix of synthetic fibers and an absorbent material. The coform web is positioned adjacent to a cellular film that includes a plurality of cavities encapsulating a gas (e.g., air). Typically, the cellular film constitutes from about 30 wt. % to about 70 wt. %, in some embodiments from about 40 wt. % to about 80 wt. %, and in some embodiments, from about 45 wt. % to about 55 wt. % of the laminate, and the coform nonwoven web constitutes from about 30 wt. % to about 70 wt. %, in some embodiments from about 40 wt. % to about 80 wt. %, and in some embodiments, from about 45 wt. % to about 55 wt. % of the laminate.

By selectively controlling various aspects of the coform web, film, and the particular manner in which the film and coform web are laminated together, the present inventors have discovered that the resulting laminate can achieve an increased bulk that remains relatively stable even in a wet condition. Thus, the resulting laminate can be readily employed in a wet wipe without losing its bulk and overall texture. The caliper (or thickness) of the laminate may, for instance, be about 0.1 centimeters or more, in some embodiments from about 0.2 to about 3 centimeters, and in some embodiments from about 0.4 to about 2 centimeters in a dry and/or wet state. The bulk of the laminate may likewise be about 10 cubic centimeters per gram ("$cm^3/g$") or more, in some embodiments from about 12 to about 180 $cm^3/g$, and in some embodiments from about 15 to about 100 $cm^3/g$ in a dry state. Such a high bulk and thickness can result in a product that is relatively easy to handle during wiping or cleaning, but yet relatively inexpensive as the use of additional material is not necessarily required to achieve the desired properties. Further, the presence of the film within the laminate structure can also result in other beneficial properties. For instance, when used in a wet wipe product, the film can inhibit the migration of the liquid solution to the bottom of the container during storage.

Various embodiments of the present invention will now be described in more detail.

I. Cellular Film

Figure 4:
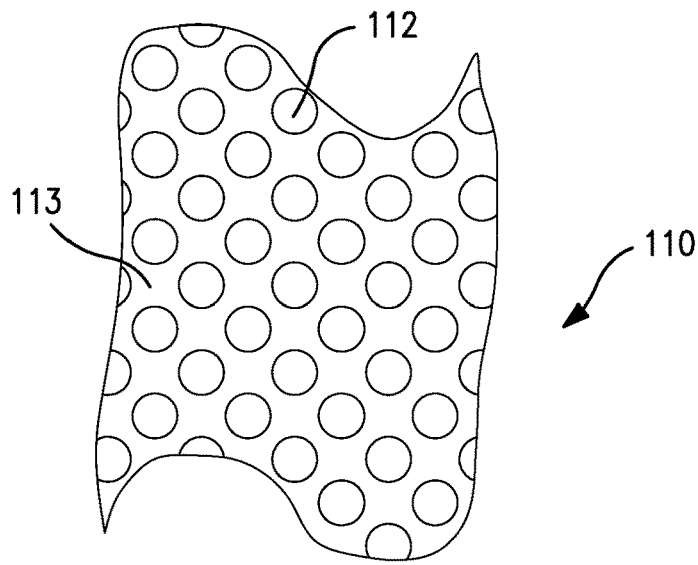
FIG. 4 is a top plan view of one embodiment of a cellular film that may be employed in the present invention.
Figure 5:
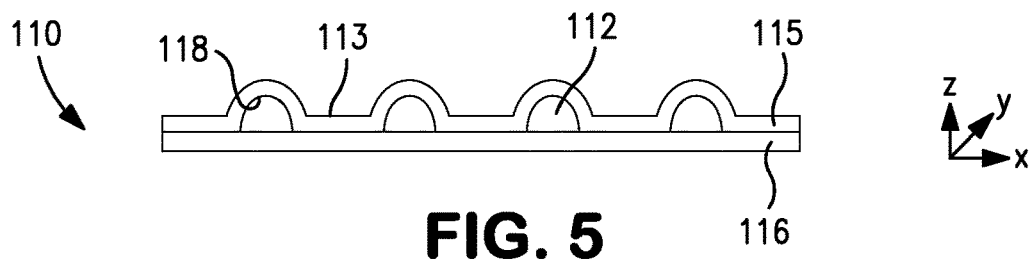
FIG. 5 is an enlarged cross-sectional view of the film of FIG. 4.

As noted above, the cellular film employed in the laminate of the present invention contains a plurality of gas-filled cavities. The film is generally formed from one or more polymers, such as polyvinyl chloride, polyvinylidene chloride, olefinic polymers (e.g., ethylene copolymers; propylene homopolymers, propylene copolymers, etc.), polyamides (e.g., nylon), etc., as well as combinations thereof. To help achieve the desired bulk and texture of the laminate structure, the size of the gas-filled cavities can be selectively controlled as desired. Referring to FIGS. 4-5, one embodiment of a cellular film 110 is shown that contains a plurality of gas-filled cavities 112 separated by land areas 113. The cavities 112 have a height in the −z direction and a width (e.g., diameter) in the −x direction. For example, the height of the cavities 112 may be from about 1 to about 25 millimeters, in some embodiments from about 2 to about 20 millimeters, and in some embodiments, from about 3 to about 15 millimeters. Likewise, the width of the cavities 112 may be from about 2 to about 60 millimeters, in some embodiments from about 3 to about 40 millimeters, and in some embodiments, from about 5 to about 20 millimeters. The distribution of the cavities along the film may vary as desired. Most desirably, however, the cavities are distributed throughout the film in a substantially homogeneous manner as shown in FIGS. 4-5.

Any of a variety of different configurations can be used to achieve the gas-filled cellular structure of the film. In the illustrated embodiment, for example, the film 110 contains a first film layer 115 and a second film layer 116 that together define the cavities 112. Although not required, the first film layer 115 may constitute from about 30 wt. % to about 70 wt. %, in some embodiments from about 40 wt. % to about 80 wt. %, and in some embodiments, from about 45 wt. % to about 55 wt. % of the film 110, while the second layer 116 may likewise constitute from about 30 wt. % to about 70 wt. %, in some embodiments from about 40 wt. % to about 80 wt. %, and in some embodiments, from about 45 wt. % to about 55 wt. % of the film 110. A plurality of spaced apart concave sections 118 are formed in the first film layer 115. The second film layer 116 is superposed onto the first film layer 115 and secured to the land areas 113 between and around the concave sections 118. Thus, the second film layer 116 covers the concave sections 118 to form the gas-filled cavities 112. Various techniques may generally be employed to secure the film layers together. Examples of some suitable methods are described, for instance, in U.S. Pat. Nos. 2,585,915; 2,776,451; 2,776,452; 3,026,231; 3,208,898; 3,285,793; 3,405,020; 3,416,984; 5,116,444; and 6,183,838. In one embodiment, for instance, the film layers are coextruded to form the cellular material in accordance with the method described in U.S. Pat. No. 5,116,444. In yet another embodiment, the film layers can simply be laminated (e.g., heat sealed) together to form the cellular film.

II. Coform Nonwoven Web

A. Synthetic Fibers

The synthetic fibers employed in the coform nonwoven web may be formed from a variety of different thermoplastic polymers as is known in the art, such as polyolefins (e.g., ethylene polymers, propylene polymers, polybutylene, etc.); polytetrafluoroethylene; polyesters (e.g., polyethylene terephthalate, polylactic acid, etc.); polyvinyl acetate; polyvinyl chloride acetate; polyvinyl butyral; acrylic resins (e.g., polyacrylate, polymethylacrylate, etc.); polyamides, (e.g., nylon); polyvinyl chloride; polyvinylidene chloride; polystyrene; polyvinyl alcohol; polyurethanes; and so forth, as well as mixtures of various polymers. Because many synthetic thermoplastic fibers are inherently hydrophobic (i.e., non-wettable), such fibers may optionally be rendered more hydrophilic (i.e., wettable) by treatment with a surfactant solution before, during, and/or after web formation. Other known methods for increasing wettability may also be employed, such as described in U.S. Pat. No. 5,057,361 to Sayovitz, et al.

The synthetic fibers may be monocomponent or multicomponent. Monocomponent fibers are generally formed from a polymer or blend of polymers extruded from a single extruder. Multicomponent fibers are generally formed from two or more polymers (e.g., bicomponent fibers) extruded from separate extruders. The polymers may be arranged in substantially constantly positioned distinct zones across the cross-section of the fibers. The components may be arranged in any desired configuration, such as sheath-core, side-by-side, pie, island-in-the-sea, three island, bull's eye, or various other arrangements known in the art. Various methods for forming multicomponent fibers are described in U.S. Pat. No. 4,789,592 to Taniguchi et al. and U.S. Pat. No. 5,336,552 to Strack et al., U.S. Pat. No. 5,108,820 to Kaneko, et al., U.S. Pat. No. 4,795,668 to Kruege, et al., U.S. Pat. No. 5,382,400 to Pike, et al., U.S. Pat. No. 5,336,552 to Strack, et al., and U.S. Pat. No. 6,200,669 to Marmon, et al. Multicomponent fibers having various irregular shapes may also be formed, such as described in U.S. Pat. No. 5,277,976 to Hogle, et al., U.S. Pat. No. 5,162,074 to Hills, U.S. Pat. No. 5,466,410 to Hills, U.S. Pat. No. 5,069,970 to Largman, et al., and U.S. Pat. No. 5,057,368 to Largman, et al.

The synthetic fibers may be formed using a variety of known processes. For example, the fibers may include spunbond fibers, meltblown fibers, as well as a combination thereof. Meltblown fibers are particularly suitable. The melt flow rate of the thermoplastic composition used to form the fibers may be selected within a certain range to optimize the properties of the resulting fibers. The melt flow rate is the weight of a polymer (in grams) that may be forced through an extrusion rheometer orifice (0.0825-inch diameter) when subjected to a force of 2160 grams in 10 minutes at 230° C. Generally speaking, the melt flow rate is high enough to improve melt processability, but not so high as to adversely interfere with the ability of the web to be laminated to the cellular film in the desired manner. Thus, in most embodiments of the present invention, the thermoplastic composition used to form the synthetic fibers has a melt flow rate of from about 200 to about 6000 grams per 10 minutes, in some embodiments from about 300 to about 3000 grams per 10 minutes, and in some embodiments, from about 400 to about 1500 grams per 10 minutes, measured in accordance with ASTM Test Method D1238-E at a load of 2160 grams at 230° C.

B. Absorbent Material

Any absorbent material may generally be employed in the coform nonwoven web, such as absorbent fibers, particles, etc. In one embodiment, the absorbent material includes fibers formed by a variety of pulping processes, such as kraft pulp, sulfite pulp, thermomechanical pulp, etc. The pulp fibers may include softwood fibers having an average fiber length of greater than 1 mm and particularly from about 2 to 5 mm based on a length-weighted average. Such softwood fibers can include, but are not limited to, northern softwood, southern softwood, redwood, red cedar, hemlock, pine (e.g., southern pines), spruce (e.g., black spruce), combinations thereof, and so forth. Exemplary commercially available pulp fibers suitable for the present invention include those available from Weyerhaeuser Co. of Federal Way, Washington under the designation "Weyco CF-405." Hardwood fibers, such as *eucalyptus*, maple, birch, aspen, and so forth, can also be used. In certain instances, *eucalyptus* fibers may be particularly desired to increase the softness of the web. *Eucalyptus* fibers can also enhance the brightness, increase the opacity, and change the pore structure of the web to increase its wicking ability. Moreover, if desired, secondary fibers obtained from recycled materials may be used, such as fiber pulp from sources such as, for example, newsprint, reclaimed paperboard, and office waste. Further, other natural fibers can also be used in the present invention, such as abaca, sabai grass, milkweed floss, pineapple leaf, and so forth. In addition, in some instances, synthetic fibers can also be utilized.

Besides or in conjunction with pulp fibers, the absorbent material may also include a superabsorbent that is in the form fibers, particles, gels, etc. Generally speaking, superabsorbents are water-swellable materials capable of absorbing at least about 20 times its weight and, in some cases, at least about 30 times its weight in an aqueous solution containing 0.9 weight percent sodium chloride. The superabsorbent may be formed from natural, synthetic and modified natural polymers and materials. Examples of synthetic superabsorbent polymers include the alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further, superabsorbents include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and so forth. Mixtures of natural and wholly or partially synthetic superabsorbent polymers may also be useful in the present invention. Particularly suitable superabsorbent polymers are HYSORB 8800AD (BASF of Charlotte, N.C. and FAVOR SXM 9300 (available from Degussa Superabsorber of Greensboro, N.C.).

The absorbent material typically constitutes from about 20 wt. % to about 95 wt. %, in some embodiments from 40 wt. % to about 90 wt. %, and in some embodiments, from about 60 wt. % to about 85 wt. % of the composite matrix. Likewise, the synthetic fibers may constitute from about 1 wt. % to about 70 wt. %, in some embodiments from 4 wt. % to about 60 wt. %, and in some embodiments, from about 5 wt. % to about 50 wt. % of the composite matrix.

The coform web may be formed using a variety of different techniques as is known in the art. Referring to FIG. 1, for example, one embodiment of an apparatus is shown that can be used to form the coform web of the present invention. Generally speaking, the apparatus employs at one meltblown die head (e.g., two) that is arranged near a chute through which the absorbent material is added while the web forms. More particularly, in the illustrated embodiment, the apparatus includes a pellet hopper 12 or 12' of an extruder 14 or 14', respectively, into which a thermoplastic composition may be introduced to form the synthetic fibers of the web. The extruders 14 and 14' each have an extrusion screw (not shown), which is driven by a conventional drive motor (not shown). As the thermoplastic composition advances through the extruders 14 and 14', it is progressively heated to a molten state due to rotation of the extrusion screw by the drive motor. Heating may be accomplished in a plurality of discrete steps with its temperature being gradually elevated as it advances through discrete heating zones of the extruders 14 and 14' toward two meltblowing dies 16 and 18, respectively. The meltblowing dies 16 and 18 may be yet another heating zone where the temperature of the thermoplastic composition is maintained at an elevated level for extrusion.

When two or more meltblowing die heads are used, such as described above, it should be understood that the fibers produced from the individual die heads may be different types of fibers. That is, one or more of the size, shape, or polymeric composition may differ, and furthermore the fibers may be monocomponent or multicomponent fibers. For example, larger fibers may be produced by the first meltblowing die head, such as those having an average diameter of about 10 micrometers or more, in some embodiments about 15 micrometers or more, and in some embodiments, from about 20 to about 50 micrometers, while smaller fibers may be produced by the second die head, such as those having an average diameter of about 10 micrometers or less, in some embodiments about 7 micrometers or less, and in some embodiments, from about 2 to about 6 micrometers. In addition, it may be desirable that each die head extrude approximately the same amount of polymer such that the relative percentage of the basis weight of the coform nonwoven web material resulting from each meltblowing die head is substantially the same. Alternatively, it may also be desirable to have the relative basis weight production skewed, such that one die head or the other is responsible for the majority of the coform web in terms of basis weight. As a specific example, for a meltblown fibrous nonwoven web material having a basis weight of 1.0 ounces per square yard or "osy" (34 grams per square meter or "gsm"), it may be desirable for the first meltblowing die head to produce about 30 percent of the basis weight of the meltblown fibrous nonwoven web material, while one or more subsequent meltblowing die heads produce the remainder 70 percent of the basis weight of the meltblown fibrous nonwoven web material. Generally speaking, the overall basis weight of the coform nonwoven web is from about 10 gsm to about 350 gsm, and more particularly from about 17 gsm to about 200 gsm, and still more particularly from about 25 gsm to about 150 gsm.

Figure 2:
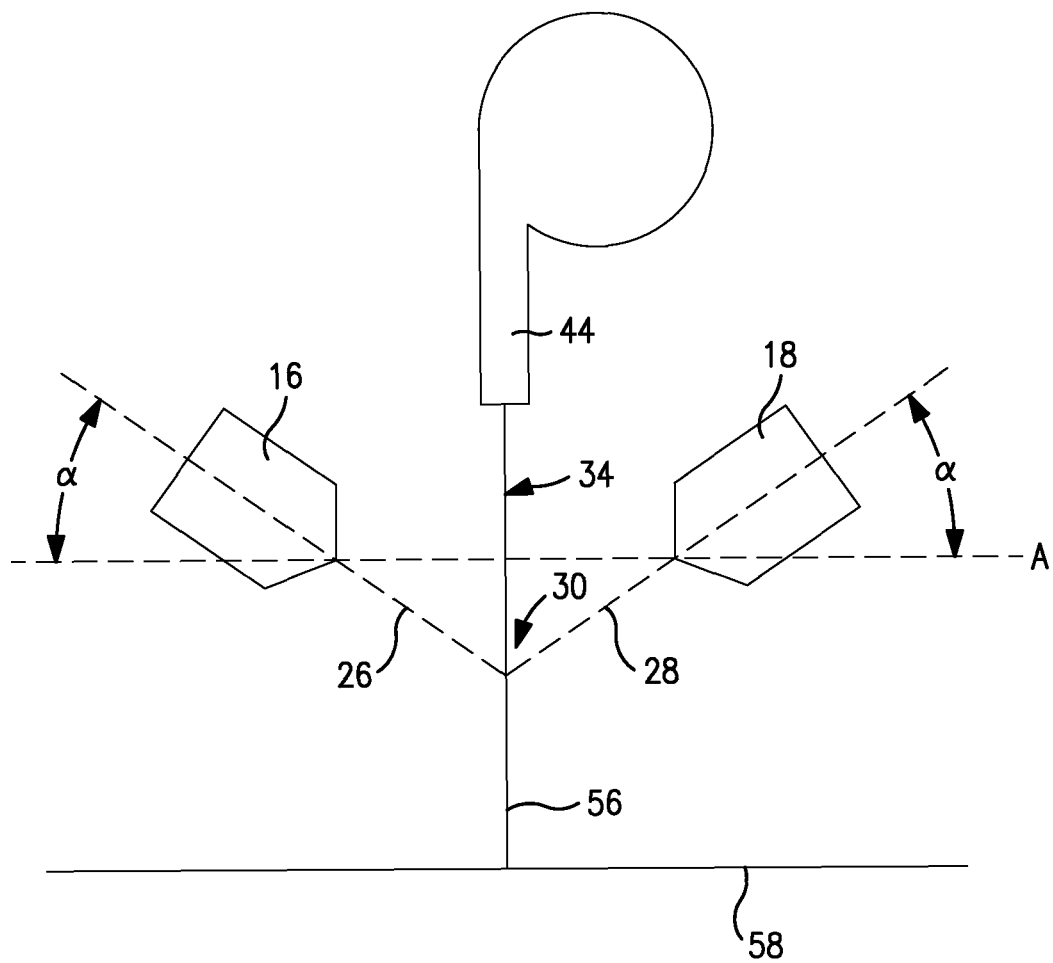
FIG. 2 is an illustration of certain features of the apparatus shown in FIG. 1.

Each meltblowing die 16 and 18 is configured so that two streams of attenuating gas per die converge to form a single stream of gas which entrains and attenuates molten threads 20 as they exit small holes or orifices 24 in each meltblowing die. The molten threads 20 are formed into fibers or, depending upon the degree of attenuation, microfibers, of a small diameter which is usually less than the diameter of the orifices 24. Thus, each meltblowing die 16 and 18 has a corresponding single stream of gas 26 and 28 containing entrained thermoplastic polymer fibers. The gas streams 26 and 28 containing polymer fibers are aligned to converge at an impingement zone 30. Typically, the meltblowing die heads 16 and 18 are arranged at a certain angle with respect to the forming surface, such as described in U.S. Pat. Nos. 5,508,102 and 5,350,624 to Georger et al. Referring to FIG. 2, for example, the meltblown dies 16 and 18 may be oriented at an angle α as measured from a plane "A" tangent to the two dies 16 and 18. As shown, the plane "A" is generally parallel to the forming surface 58 (FIG. 1). Typically, each die 16 and 18 is set at an angle ranging from about 30 to about 75 degrees, in some embodiments from about 35° to about 60°, and in some embodiments from about 45° to about 55°. The dies 16 and 18 may be oriented at the same or different angles. In fact, the texture of the coform web may actually be enhanced by orienting one die at an angle different than another die.

Referring again to FIG. 1, an absorbent material 32 (e.g., pulp fibers) is added to the two streams 26 and 28 of thermoplastic polymer fibers 20, and at the impingement zone 30. Introduction of the absorbent material 32 into the two streams 26 and 28 of thermoplastic polymer fibers 20 is desirably gradual in nature. This may be accomplished by merging a secondary gas stream 34 containing the absorbent material 32 between the two streams 26 and 28 of thermoplastic polymer fibers 20 so that all three gas streams converge in a controlled manner. Because they remain relatively tacky and semi-molten after formation, the meltblown fibers 20 may simultaneously adhere and entangle with the absorbent material 32 upon contact therewith to form a coherent nonwoven structure.

Any conventional equipment may be employed to supply the absorbent material. In the illustrated embodiment, for instance, a picker roll 36 arrangement is provided that has a plurality of teeth 38 adapted to separate a mat or batt 40 of the absorbent material into individual fibers. When employed, the sheets or mats 40 are fed to the picker roll 36 by a roller arrangement 42. After the teeth 38 of the picker roll 36 have separated the mat into separate fibers, they are conveyed toward the stream of thermoplastic polymer fibers through a nozzle 44. A housing 46 encloses the picker roll 36 and provides a passageway or gap 48 between the housing 46 and the surface of the teeth 38 of the picker roll 36. A gas, for example, air, is supplied to the passageway or gap 46 between the surface of the picker roll 36 and the housing 48 by way of a gas duct 50. The gas duct 50 may enter the passageway or gap 46 at the junction 52 of the nozzle 44 and the gap 48. The gas is supplied in sufficient quantity to serve as a medium for conveying the absorbent material 32 through the nozzle 44. The gas supplied from the duct 50 also serves as an aid in removing any remaining absorbent material 32 from the teeth 38 of the picker roll 36. The gas may be supplied by any conventional arrangement such as, for example, an air blower (not shown).

The absorbent material 32 is typically conveyed through the nozzle 44 at about the velocity at which the absorbent material 32 leaves the teeth 38 of the picker roll 36. In other words, the absorbent material 32, upon leaving the teeth 38 of the picker roll 36 and entering the nozzle 44, generally maintains its velocity in both magnitude and direction from the point where they left the teeth 38 of the picker roll 36. Such an arrangement, which is discussed in more detail in U.S. Pat. No. 4,100,324 to Anderson, et al.

If desired, the velocity of the secondary gas stream 34 may be adjusted to achieve coform structures of different properties. For example, when the velocity of the secondary gas stream is adjusted so that it is greater than the velocity of each stream 26 and 28 of thermoplastic polymer fibers 20 upon contact at the impingement zone 30, the absorbent material 32 is incorporated in the coform nonwoven web in a gradient structure. That is, the absorbent material 32 has a higher concentration between the outer surfaces of the coform nonwoven web than at the outer surfaces. On the other hand, when the velocity of the secondary gas stream 34 is less than the velocity of each stream 26 and 28 of thermoplastic polymer fibers 20 upon contact at the impingement zone 30, the absorbent material 32 is incorporated in the coform nonwoven web in a substantially homogenous fashion. That is, the concentration of the absorbent material is substantially the same throughout the coform nonwoven web. This is because the low-speed stream of absorbent material is drawn into a high-speed stream of thermoplastic polymer fibers to enhance turbulent mixing which results in a consistent distribution of the absorbent material.

To convert the composite stream 56 of thermoplastic polymer fibers 20 and absorbent material 32 into a coform nonwoven structure 54, a collecting device may be located in the path of the composite stream 56. The collecting device may be a forming surface 58 (e.g., belt, drum, wire, fabric, etc.) driven by rollers 60 and that is rotating as indicated by the arrow 62 in FIG. 1. The merged streams of thermoplastic polymer fibers and absorbent material are collected as a coherent matrix of fibers on the surface of the forming surface 58 to form the coform nonwoven web 54. If desired, a vacuum box (not shown) may be employed to assist in drawing the near molten meltblown fibers onto the forming surface 58. The resulting textured coform structure 54 is coherent and may be removed from the forming surface 58 as a self-supporting nonwoven material.

It should be understood that the present invention is by no means limited to the above-described embodiments. In an alternative embodiment, for example, first and second meltblowing die heads may be employed that extend substantially across a forming surface in a direction that is substantially transverse to the direction of movement of the forming surface. The die heads may likewise be arranged in a substantially vertical disposition, i.e., perpendicular to the forming surface, so that the thus-produced meltblown fibers are blown directly down onto the forming surface. Such a configuration is well known in the art and described in more detail in, for instance, U.S. Patent Application Publication No. 2007/0049153 to Dunbar, et al. Furthermore, although the above-described embodiments employ multiple meltblowing die heads to produce fibers of differing sizes, a single die head may also be employed. An example of such a process is described, for instance, in U.S. Patent Application Publication No. 2005/0136781 to Lassiq, et al.

III. Lamination

Figure 6:
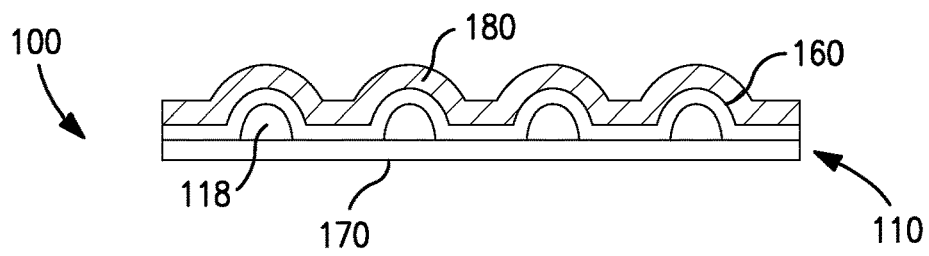
FIG. 6 is an enlarged cross-sectional view of one embodiment of the laminate of the present invention.
Figure 7:
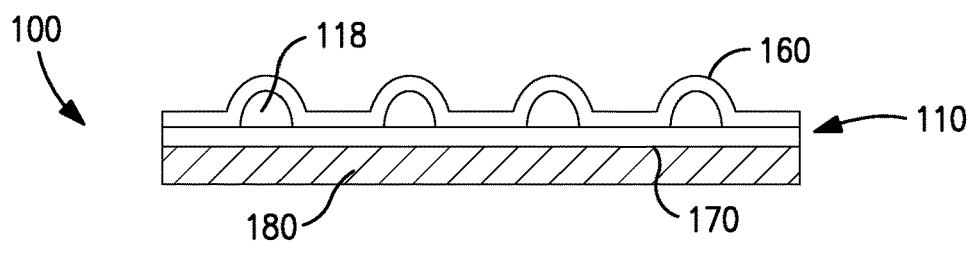
FIG. 7 is an enlarged cross-sectional view of another embodiment of the laminate of the present invention.

The manner in which the cellular film and coform nonwoven web are combined together may vary as desired. In one embodiment, for example, the coform web may be laminated to the textured surface of the film that is formed by the gas-filled cavities. One example of such a laminate is shown in FIG. 6 as element 100. As shown, the laminate 100 contains a film 110 having a textured surface 160 formed by gas-filled cavities 118 and a relatively flat surface 170. The surfaces 160 and 170 may be formed from one or multiple layers as described above. In this particular embodiment, a coform nonwoven web 180 is laminated to the textured surface 160 of the film 110. Of course, in other embodiments, the coform web may be laminated to the relatively flat surface of the film. In FIG. 7, for instance, the coform nonwoven web 180 is laminated to the relatively flat surface 170 of the film 110. Of course, it should also be understood that both surfaces may be textured if so desired. Further, it should also be understood that multiple coform webs and/or films may be employed in the laminate of the present invention. In one embodiment, for example, multiple coform webs may be employed such that the film is positioned adjacent to and between at least two coform webs.

Regardless of the particular configuration, various lamination methods can be employed in the present invention to adhere the coform web to the cellular film. In certain embodiments, for example, the coform web may be laminated to a surface (e.g., texture surface and/or relatively flat surface) of the cellular film after it has been formed. This may be accomplished using conventional laminate techniques. Alternatively, the coform web may be deposited onto the film as the fibers are formed. Referring again to FIGS. 1-2, for instance, a cellular film (not shown) may be disposed onto the forming surface 58. In this manner, the merged streams of synthetic fibers and absorbent material can be collected as a coherent matrix of fibers on the surface of the cellular film to form the laminate structure. To aid in such fiber deposition, a portion of the film may be perforated is so desired. To avoid interference with the encapsulated cavities, such perforation may occur in areas between the cavities. If desired, a vacuum box (not shown) may also be employed to assist in drawing the fibers onto the film surface.

The coform web may also be laminated to the cellular film as it is being formed using a technique such as described in U.S. Pat. No. 6,183,838 to Kannankeril. For example, a first film layer may be placed into contact with a patterned embossing roll and a suctional force may be applied to bias the film layer against the patterned surface of the roll and thereby form a plurality of concave sections therein. The suctional force may be achieved in a variety of ways (e.g., vacuum slots, shoes, rolls, etc.). The amount of suctional force may be selectively controlled to enhance bonding without significantly deteriorating the integrity of the layers. For example, pneumatic vacuum pressure may be employed to apply the suctional force that is about 3 kilopascals or more, in some embodiments about 15 kilopascals or more, and in some embodiments, from about 30 to about 100 kilopascals. In any event, a second film layer may also be placed into contact with the first layer on the embossing roll so that the layers are bonded together over their contiguous surfaces. In this manner, a gas (e.g., air) can become entrapped within the concave section to form the cavities. During this process, the coform web may also be supplied (e.g., from a roll) onto the embossing roll into a superposed relation with the second film layer so that it is capable of bonding thereto.

In the embodiments described above, the first and second film layers are derived from a single film containing such layers. In other embodiments, however, the layers of the cellular film can be derived from separate materials. In one embodiment, for instance, a first laminate may be formed that contains a first coform nonwoven web positioned adjacent to a first film layer, which may be initially relatively flat in nature. The first laminate (e.g., surface defined by the coform nonwoven web) may be placed into contact with a patterned embossing roll and applied with a suctional force to bias the first laminate against the roll and form a plurality of concave sections in the first film layer. A second laminate, which may contain a second coform nonwoven web positioned adjacent to a second film layer, may be brought into contact with the first film layer to entrap a gas in the concave sections and form cavities that encapsulate a gas. The resulting nonwoven laminate thus contains a cellular film formed from the combination of the first and second film layers, which are both positioned between the coform nonwoven webs of the respective first and second laminates.

Figure 3:
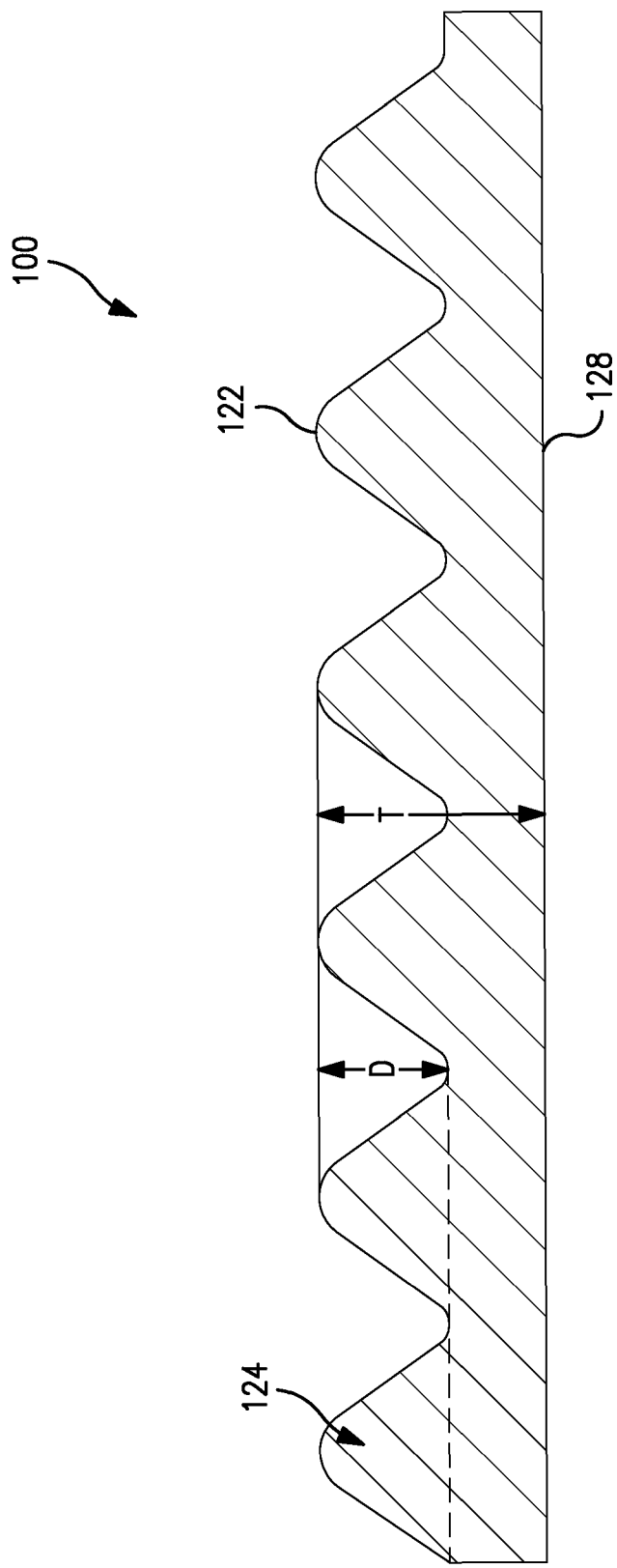
FIG. 3 is a cross-sectional view of one embodiment of a textured laminate structure that may be formed in accordance with the present invention.

Regardless of the particular method employed, the resulting nonwoven laminate may have a bulky feel and textured surface due to the presence of the cellular film. Depending on the distribution of the gas-filled cavities, the texture may be substantially uniform or it may vary in a patterned configuration across a surface of the laminate. In most embodiments, for instance, the cavities are spaced apart within the laminate structure and thus create a patterned surface texture that has the appearance of peaks or tufts. Because the peaks are created by gas-filled cavities, the surface thus has a desirable resiliency useful for wiping and scrubbing. Referring to FIG. 3, for instance, a cross section of a laminate 100 having a first exterior surface 122 and a second exterior surface 128 is shown. In this embodiment, the first exterior surface 122 has a three-dimensional surface texture that includes peaks 124 extending upwardly from the plane of the laminate. One indication of the magnitude of three-dimensionality in the textured exterior surface(s) of the laminate is the peak to valley ratio, which is calculated as the ratio of the overall caliper "T" divided by the valley depth "D." When formed in accordance with the present invention, the coform web typically has a peak to valley ratio of about 1.1 to about 10, in some embodiments from about 1.5 to about 6, and in some embodiments, from about 2 to about 4. The number and arrangement of the peaks 24 may vary widely depending on the desired end use. Generally, the textured coform web will have from about 0.05 and about 4 peaks per square centimeter, and in some embodiments, from about 0.2 and 1 peaks per square centimeter. The coform web may also exhibit a three-dimensional texture on the second surface of the web. In this case, the valley depth D is measured for both exterior surfaces as above and are then added together to determine an overall material valley depth.

IV. Articles

The nonwoven laminate may be used in a wide variety of articles. For example, the laminate may be incorporated into an "absorbent article" that is capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, mitt wipe, and so forth; medical absorbent articles, such as garments, fenestration materials, underpads, bedpads, bandages, absorbent drapes, and medical wipes; food service wipers; clothing articles; pouches, and so forth. Materials and processes suitable for forming such articles are well known to those skilled in the art.

In one particular embodiment of the present invention, the nonwoven laminate is used to form a wipe. The wipe may be formed entirely from the laminate or it may contain other materials, such as films, nonwoven webs (e.g., spunbond webs, meltblown webs, carded web materials, other coform webs, airlaid webs, etc.), paper products, and so forth. In one embodiment, for example, two layers of material may be attached together to form the wipe, such as described in U.S. Patent Application Publication No. 2007/0065643 to Kopacz. In such embodiments, one or both of the layers may be formed from the laminate of the present invention. In another embodiment, it may be desired to provide a certain amount of separation between a user's hands and a moistening or saturating liquid that has been applied to the wipe, or, where the wipe is provided as a dry wiper, to provide separation between the user's hands and a liquid spill that is being cleaned up by the user. In such cases, an additional nonwoven web or film may be attached to a surface of the laminate to provide physical separation and/or provide liquid barrier properties. Other fibrous webs may also be included to increase absorbent capacity, either for the purposes of absorbing larger liquid spills, or for the purpose of providing a wipe a greater liquid capacity. When employed, such additional materials may be attached to the laminate using any method known to one skilled in the art, such as by thermal or adhesive lamination or bonding with the individual materials placed in face to face contacting relation. Regardless of the materials or processes utilized to form the wipe, the basis weight of the wipe is typically from about 20 to about 200 grams per square meter (gsm), and in some embodiments, between about 35 to about 100 gsm. Lower basis weight products may be particularly well suited for use as light duty wipes, while higher basis weight products may be better adapted for use as industrial wipes.

The wipe may assume a variety of shapes, including but not limited to, generally circular, oval, square, rectangular, or irregularly shaped. Each individual wipe may be arranged in a folded configuration and stacked one on top of the other to provide a stack of wet wipes. Such folded configurations are well known to those skilled in the art and include c-folded, z-folded, quarter-folded configurations and so forth. For example, the wipe may have an unfolded length of from about 2.0 to about 80.0 centimeters, and in some embodiments, from about 10.0 to about 25.0 centimeters. The wipes may likewise have an unfolded width of from about 2.0 to about 80.0 centimeters, and in some embodiments, from about 10.0 to about 25.0 centimeters. The stack of folded wipes may be placed in the interior of a container, such as a plastic tub, to provide a package of wipes for eventual sale to the consumer. Alternatively, the wipes may include a continuous strip of material which has perforations between each wipe and which may be arranged in a stack or wound into a roll for dispensing. Various suitable dispensers, containers, and systems for delivering wipes are described in U.S. Pat. No. 5,785,179 to Buczwinski, et al.; U.S. Pat. No. 5,964,351 to Zander; U.S. Pat. No. 6,030,331 to Zander; U.S. Pat. No. 6,158,614 to Haynes, et al.; U.S. Pat. No. 6,269,969 to Huang, et al.; U.S. Pat. No. 6,269,970 to Huang, et al.; and U.S. Pat. No. 6,273,359 to Newman, et al.

In certain embodiments of the present invention, the wipe is a "wet" or "premoistened" wipe in that it contains a liquid solution for cleaning, disinfecting, sanitizing, etc. The particular liquid solutions are not critical and are described in more detail in U.S. Pat. No. 6,440,437 to Krzysik, et al.; U.S. Pat. No. 6,028,018 to Amundson, et al.; U.S. Pat. No. 5,888,524 to Cole; U.S. Pat. No. 5,667,635 to Win, et al.; and U.S. Pat. No. 5,540,332 to Kopacz, et al. The amount of the liquid solution employed may depending upon the type of wipe material utilized, the type of container used to store the wipes, the nature of the cleaning formulation, and the desired end use of the wipes. Notably, the present inventors have discovered that the laminate of the present invention can employ even lower amounts of solution than conventionally employed. For example, each wipe may contain from about 100 wt. % to about 500 wt. %, in some embodiments from about 200 wt. % to about 450 wt. %, and in some embodiments, from about 250 to about 400 wt. % of a liquid solution based on the dry weight of the wipe.

The present invention may be better understood with reference to the following examples.

Test Methods

Caliper: The term "caliper" generally refers to the thickness of a sheet or web. Caliper can be measured using a sample size of 90 by 102 mm millimeters under a controlled loading pressure of approximately 0.345 kilopascal (kPa) [0.05 pound-force per square inch (psi)]. The thickness is determined as the distance between an anvil, or base, and a platen used to apply the specified pressure.

Example 1

A coform web was made by fiberizing Golden Isles Fluff Pulp (GP Cellulose, LLC) in an arrangement similar to that described in FIG. 1. The pulp was fed at a rate of 29.8 g per cross sectional inch per min with an air flow rate of 9900 ft/min through a nozzle. A propylene homopolymer (Metocene™ MF650X, Equistar Chemicals, LP) was used to form meltblown fibers and introduced to the cellulose fibers at a 45° angle at a rate of 12.8 g per cross sectional inch per min with an air velocity of 34 ft/min from each meltblown head. The coform web thus formed is laminated to a cellular film (38 grams per square meter) containing a flat film layer and textured film layer with cavities having a diameter of approximately 1 centimeter. The cavities were relatively uniformly distributed with a distribution of approximately 0.416 cavities per square centimeter and the cavity height was approximately 3.3 millimeters. An adhesive was sprayed onto one surface of the encapsulated film and the coform layer was then placed thereon and passed through a nip roll with 2 psi pressure. Finally, a second coform nonwoven web was laminated to the other side of film in the manner described above.

Example 2

A laminate (as described in Example 1) was perforated with 0.8 millimeter diameter holes distributed uniformly across the laminate with a hole density of 0.104 holes per square centimeter and each holes were on locations where there was an encapsulated bubble. One side of the perforated laminate was sprayed with an adhesive and placed on a moving forming surface such that the adhesive surface faces the nozzle, such as shown in FIG. 1. A coform nonwoven web was then formed on to the surface as described in Example 1. Another adhesive was then sprayed on the other side of film laminate and a layer of coform was formed on that surface by passing that under coform head a second time.

The resulting laminate was tested under dry and wet conditions. Wet samples were made by adding an aqueous solution in an amount of 300% by weight of the laminate. The aqueous solution contained 99.2 wt. % of water and 0.8 wt. % of a surfactant. The dry and wet thickness values were then measured and are set forth in the table below.

|  | Dry Thickness (mm) | Wet Thickness (mm) |
| --- | --- | --- |
| Example 1 | 4.7 | 4.1 |
| Example 2 | 5.2 | 4.4 |

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A nonwoven laminate comprising:
   a cellular film containing a plurality of spaced apart cavities that encapsulate a gas, wherein the cellular film contains a first film layer and a second film layer and wherein a plurality of concave sections are formed in the first film layer and the second film layer is flat, wherein the cavities have a height of from about 1 to about 25 millimeters;
   a coform nonwoven web positioned adjacent to the cellular film, wherein the coform nonwoven web comprises a composite matrix formed from a combination of synthetic fibers and an absorbent material;
   wherein the laminate defines an exterior surface having a three-dimensional texture that includes a plurality of peaks and valleys, wherein the peaks and valleys have a peak to valley ratio of about 1.5 to about 6.

2. The nonwoven laminate of claim 1, wherein the caliper of the laminate is about 0.1 centimeters or more.

3. The nonwoven laminate of claim 1, wherein the cavities are spaced apart by land areas.

4. The nonwoven laminate of claim 1, wherein the cavities have a width of from about 2 to about 60 millimeters.

5. The nonwoven laminate of claim 1, wherein the coform nonwoven web is positioned adjacent to the first film layer, the second film layer, or both.

6. The nonwoven laminate of claim 1, wherein the synthetic fibers are meltblown fibers.

7. The nonwoven laminate of claim 6, wherein the meltblown fibers contain a polyolefin.

8. The nonwoven laminate of claim 1, wherein the absorbent material contains pulp fibers.

9. The nonwoven laminate of claim 1, wherein the synthetic fibers constitute from 1 wt. % to about 70 wt. % of the coform nonwoven web and the absorbent material constitutes from about 20 wt. % to about 95 wt. % of the coform nonwoven web.

10. The nonwoven laminate of claim 1, wherein the cellular film constitutes from about 30 wt. % to about 70 wt. % of the laminate and the coform nonwoven web constitutes from about 30 wt. % to about 70 wt. % of the laminate.

11. The nonwoven laminate of claim 1, wherein the film has a textured surface defined by the cavities, the coform nonwoven web being positioned adjacent to the textured surface.

12. A wipe comprising the nonwoven laminate of claim 1.

13. The wipe of claim 12, wherein the wipe contains from about 100 to about 500 wt. % of a liquid solution based on the dry weight of the wipe.

14. The nonwoven laminate of claim 1, wherein the cavities have a height from about 15 to about 25 millimeters and a width from about 5 to about 60 millimeters.

15. The nonwoven laminate of claim 1, wherein the peaks and valleys have a peak to valley ratio of about 2 to about 4.

16. The nonwoven laminate of claim 1, comprising from about 0.05 to about 1 peak per square centimeter.

17. The nonwoven laminate of claim 1, comprising:
   an adhesive between the cellular film and the coform nowoven web.

18. The nonwoven laminate of claim 1, wherein the first film layer constitutes from about 30 wt. % to about 70 wt. % of the cellular film and the second film layer constitutes from about 30 wt. % to about 70 wt. % of the cellular film.

19. The nonwoven laminate of claim 1, wherein the bulk of the laminate is about 10 cubic centimeters per gram or more.

* * * * *